(12) United States Patent
Leonhardt

(10) Patent No.: US 6,885,881 B2
(45) Date of Patent: Apr. 26, 2005

(54) DEVICE FOR MEASURING HUMAN BLOOD SUGAR LEVELS

(76) Inventor: Steffen Leonhardt, Arnimstrasse 10b, D-23566, Lübeck (DE)

( * ) Notice: Subject to any disclaimer, the term of this patent is extended or adjusted under 35 U.S.C. 154(b) by 0 days.

(21) Appl. No.: 10/038,773

(22) Filed: Jan. 8, 2002

(65) Prior Publication Data

US 2002/0128543 A1 Sep. 12, 2002

Related U.S. Application Data

(63) Continuation of application No. PCT/EP99/04823, filed on Jul. 8, 1999.

(51) Int. Cl.[7] .................................................. A61B 5/00
(52) U.S. Cl. .......................... 600/316; 600/322; 600/342
(58) Field of Search ................................. 600/319, 326, 600/322, 327, 365, 316, 309–310, 342

(56) References Cited

U.S. PATENT DOCUMENTS

| | | |
|---|---|---|
| 3,837,339 A | 9/1974 | Aisenberg et al. |
| 4,623,248 A * | 11/1986 | Sperinde .................... 356/41 |
| 4,704,029 A | 11/1987 | Van Heuvelen |
| 4,763,655 A * | 8/1988 | Wirtzfeld et al. ............. 607/22 |
| 4,900,303 A | 2/1990 | Lemelson |
| 4,975,581 A | 12/1990 | Robinson et al. |
| 4,979,509 A | 12/1990 | Hakky |
| 5,048,524 A | 9/1991 | Bailey |
| 5,146,091 A | 9/1992 | Knudson |
| 5,333,609 A * | 8/1994 | Bedingham et al. ......... 600/339 |
| 5,404,877 A * | 4/1995 | Nolan et al. ................. 600/484 |

FOREIGN PATENT DOCUMENTS

| | | | |
|---|---|---|---|
| DE | 3736092 | 5/1989 | |
| EP | 0554955 A | 11/1993 | |
| JP | 08-029699 | * 2/1996 | ............ A61B/1/00 |
| WO | WO 91/18548 | 12/1991 | |

* cited by examiner

Primary Examiner—Eric F. Winakur
Assistant Examiner—Matthew Kremer
(74) Attorney, Agent, or Firm—Shlesinger, Arkwright & Garvey LLP

(57) ABSTRACT

Device for measuring human blood sugar levels with a catheter, the free end of which is positioned in a blood vessel, wherein the catheter consists of at least one optical waveguide comprising a light source for coupling light into the at least one optical waveguide, a measurement point at the free end of the catheter at which point the light is emitted from the at least one optical waveguide, wherein the light is dispersed by the blood and/or transmitted by the blood and wherein the dispersed and/or transmitted light is coupled again into the minimum of one return optical waveguide, a detector to receive the light which is returned, and a computer unit for analysing the light received by the detector. Provision is made for a cleansing device to be located at the point of measurement for removing the tissue particles deposited from the blood in order to provide a device which is as accurate as possible and which delivers constant measurement values over time for blood sugar levels which can be used as the basis for further data analysis.

42 Claims, 6 Drawing Sheets

DEVICE FOR MEASURING HUMAN BLOOD SUGAR LEVELS

RELATED APPLICATIONS

This application is a continuation of International Application No. PCT/EP99/04823, filed Jul. 8, 1999.

FIELD OF THE INVENTION

The invention refers to a device for measuring human blood sugar levels with a catheter, the free end of which is positioned in a blood vessel, with the catheter comprising at least one optical waveguide, a light source for coupling light into the at least one optical waveguide, a measurement point at the free end of the catheter where the light from the at least one optical waveguide emerges from the optical waveguide, wherein the light is dispersed by the blood and/or conducted by the blood and wherein the dispersed and/or conducted light is coupled back into at least one return optical waveguide with a detector to receive the returned light and with a computer unit to evaluate the light received by the detector.

BACKGROUND OF THE INVENTION

Physiologically, human blood sugar levels are maintained at a constant level within certain boundaries (60 . . . 120 mg/dl fasting at rest). Blood sugar levels are influenced by the following four hormones via the hormonal feedback control system:

Insulin (formed in the beta cells of the pancreas)
Glucagon (formed in the alpha cells of the pancreas)
Adrenaline (formed in the adrenal medulla)
Glucocorticoids (e.g. cortisol, formed in the adrenal cortex).

While glucagon increases blood sugar levels by reducing glycogen reserves in the liver, insulin lowers blood sugar levels by transferring the sugar from the blood into the various body cells. Adrenaline (during sport) and cortisol (during stress) have a slower effect and also increase blood sugar levels. Consequently, insulin is the only hormone which reduces blood sugar levels. FIG. 1 shows schematically how insulin and glucagon affect blood sugar levels.

Diabetes mellitus is characterised by a relative or absolute lack of insulin, e.g. due to the destruction of beta cells as a result of an auto-immune disease (Type I) or due to the loss of insulin efficacy (insulin resistance, Type II). Consequently, the control of blood sugar levels is hampered, resulting in an increase in the mean blood sugar level. External glucose input (e.g. intake of food) or the internal supply of glucose (adrenaline, cortisol) cannot be adequately corrected for diabetics, allowing this to be used in the diagnosis of diabetes mellitus.

As part of modern standard treatment methods, blood sugar levels are determined with the aid of blood from a finger taken one or more times a day employing enzymatic chemical methods using a test strip. FIG. 2 shows a schematic representation of such a testing device.

In addition to dietary measures (compensatory reduction of external sugar intake), attempts can be made to regulate blood sugar levels using medication (e.g. using sulfonylurea to stimulate increased insulin production) or by means of subcutaneous injection of insulin into physiological tracts. Injection aides or mechanical pumps exist for continuously injecting insulin.

The blood sugar levels of most diabetics is poorly regulated as a result of the often insufficient frequency of measurement and the lack of an opportunity to respond adequately to disruptions. In the case of chronic to high blood sugar levels, subsequent damage occurs, particularly to nerves and vessels, which can lead to drastic consequences (arteriosclerosis, heart attack, amputations, blindness, obligatory dialysis due to renal failure etc.).

Various treatment approaches are currently at an experimental stage, aiming to close the blood glucose control loop adequately with acceptable control quality. One differentiates between "biological" and "technical" approaches.

With the biological approach an attempt is made to utilise the natural functions of donated islet cells as sensors and actuators. Entire pancreas transplants (approx. 100 p.a. in Germany) and the transplantation of isolated donor islet cells (approx. 20 p.a. in Germany) are used clinically.

Both these procedures have a limited prospect of success due to the approximately constant number of donors which is to low, the necessity of immune suppression with its risk of infection, the risk of the genesis of malignant tumours and high medication costs.

The use of the unlimited supply of animal islet cells is restricted by the even stronger immune reaction.

The technical approaches attempt to close the defective control loop by employing technical means.

It is known that insulin pumps (e.g. roller or piston pumps) can be used as actuators which can be operated externally as well as in the form of implants. FIG. 3 shows an insulin pump attached to a patient.

The core problem for all technical treatment approaches is the reliable, comfortable and painless determination of blood sugar levels as continuously as possible. It is known that chemical procedures can be used as blood sugar sensors, e.g. enzymatic procedures such as glucose oxidase (GOD) reaction, in some cases in combination with ultrafiltration/microdialysis, or electrocatalytic procedures (direct oxidation of glucose on platinum electrodes). It is also known that these methods can be miniaturised and sometimes implanted. For instance, implantable prototypes for microdialysis sensors with GOD reaction exist ("Ulm "Sugar Watch System""). The main difficulty for all chemical sensor approaches is their short service life (<3 weeks).

A device of this type known from U.S. Pat. No. 4,975,581. In order to measure the blood sugar level, the catheter is externally inserted into an arm vein, whereby provision is made for a connection to an insulin pump which introduces into the body the amount of insulin calculated on the basis of an evaluation of the light dispersed by the blood.

Following this procedure, the catheter must be removed from the arm vein. This device has the disadvantage that the injection area can become inflamed from the catheter having to be inserted frequently. Moreover, the mobility of the patient is still severely restricted with this method. A corresponding procedure involving the blood sugar concentration being determined by evaluating the polarisation of light is known from DE 195 40 456 C2.

U.S. Pat. No. 4,704,029 makes known a combinatory approach for measuring blood sugar content by evaluating the absorption, reflection and polarisation of light by the blood. In principle, this device is implantable. However, a major problem is the fact that the measurement interface becomes so contaminated from deposition that the measured values cannot be used.

DE 37 36 092 A1 makes known a measuring device for continually determining the concentration of the blood sugar content in a measurement cuvette, whereby the blood sugar concentration is determined by determining the optical rotation by polarizers and analysers. A corresponding device using the analysis of the reflection of the light by the blood is known from WO 97/28437.

WO 91/18548 makes known a device whereby the blood sugar level is determined externally through the skin and which involves two infrared wavelengths being transmitted and received, with the absorption of the wavelengths being analysed. However, the accuracy of these non-invasive "in vivo" measurements is not sufficient for clinical usage owing to the absorption by the skin and mucous membrane cells. A procedure of this nature for evaluating a test beam and a reference beam is known from U.S. Pat. No. 5,146,091.

OBJECTS AND SUMMARY OF THE INVENTION

The aim of the invention is to provide a device of this generic type which can supply blood sugar content measurement values which are as accurate as possible and which deliver temporally stable values which can be used as the basis for further data processing.

The solution in accordance with the invention is characterised by the provision of a cleansing device at the point of measurement designed to remove the tissue particles deposited from the blood. The invention is thus based on the fact that measurement is severely hampered by the blood's ongoing immune response processes. The immune response for instance, causes indestructible foreign bodies to be encapsulated by endogenous tissue. The invention allows this endogenous tissue to be removed prior to measurement, with the cleansing of the point of measurement being either continual or intermittent. In order for cleansing to be intermittent, the function of the cleansing device can be controlled from the computer unit.

In accordance with a preferred embodiment provision is made for the cleansing device comprising a flushing device which washes the point of measurement with a flushing fluid. The flushing fluid can, for instance, consist of a physiologic sodium chloride solution. For this purpose, outlets are located directly in front of the measurement window. After flushing a sufficient period of time should be allowed to pass before the next measurement is taken.

In another preferred embodiment provision is made for the cleansing device comprising a controllable actuator which clears or wipes free the light emission orifice of the minimum of one optical waveguide when triggered. For instance, cleansing can occur by means of the relative movement of a form-fitting body against the point of measurement. For instance, the actuator can consist of a piston which is inserted into a perfectly fitted opening located at the free end of the catheter and which is moved between a position where it forms a seal flush with the catheter surface and a position where it fits into a recess positioned opposite the catheter surface, wherein in the recessed position it frees a light emission orifice of the minimum of one optical waveguide. In doing so, the piston can be inserted into the catheter radially or axially.

A shape memory alloy, a thermopneumatic drive, a piezoelectric drive or a rotor can be considered for the drive element. If the actuator can be triggered, the control line can consist of a hydraulic or pneumatic line which is effectively linked to the piston, wherein a linear actuator for imparting pressure on the control line is integrated into the implanted housing. The piston can, for instance, be actuated by a micromotor with a crank drive, in which case the control line can consist of an electrical control line. It is also conceivable that the piston be actuated by a lifting magnet.

In accordance with another preferred embodiment provision is made for a cleansing device which is a controllable ultrasonic generator which transmits ultrasonic or shock waves when activated in such a manner that the light emission orifice of the minimum of one optical waveguide is freed of deposition when activated.

In accordance with a further preferred embodiment, provision is made for a cleansing device which comprises an electrostatic unit for generating electrostatic power with which a specified charge is delivered to the point of measurement.

In accordance with a further preferred embodiment, provision can be made for a cleansing device which comprises a unit for generating high-energy lightwaves which provides for specified local tissue particles to be vaporised. The optical waveguide itself can be used effectively for generating high-energy lightwave radiation. However, additional optical waveguides are also possible within the catheter.

The energy required for control purposes can be supplied to the point of measurement in electrical, thermal, optic, mechanical, hydraulic or pneumatic form, Measurements can be undertaken at the point of measurement by employing transmission, that is on the basis of transmission across a specified sampling length, or on the basis of diffuse reflection from the surface of the catheter. In the case of transmission, as a rule it will be necessary to make provision for an optical input waveguide and an optical output waveguide, wherein the optical path between the optical input and the optical output waveguides is interrupted at the point of measurement for measurement purposes. In the case of transmission measurement, the point of measurement is typically cleansed between two optical waveguide segments. In the case of reflective measurement, the cleansing device is located anterior to the optical output and input point (optical measurement).

The catheter is clad with a biocompatible material for reasons of medical compatibility. The catheter contains at least one optical waveguide, wherein the catheter and the optical waveguide can be a single piece of solid material. The cladding is interrupted or has an aperture at the point of measurement.

In accordance with another preferred embodiment provision is made for the light source, the detector and the computer unit to be integrated into an implant together with an energy store for the voltage supply. The point of measurement in the blood is thus spatially separated from the actual optical measurement device and optically connected by means of the optical waveguide inside the catheter.

In accordance with a further preferred embodiment provision is made for a telemetry unit to be integrated into the implant, with which it is possible by using a probe provided for this purpose to transmit data and/or energy between the computer unit and a control unit located outside the body. The telemetry unit and the probe could for instance each have an oscillating circuit with an inductor, wherein the oscillating circuit on the side of the telemetry unit and the oscillating circuit on the side of the probe can be tuned for the purpose of transmitting data. In this way, data can be transmitted without direct contact by inductively coupling the inductors. It is particularly effective if the energy content of the frequency transmitted from the control unit to the telemetry unit charges an accumulator or a condenser in order to provide energy to the implant.

The devices in accordance with the invention can be regulated, wherein the measured values are transmitted to a control unit located outside the body by a telemetry unit, and have an extracorporeal insulin pump for injecting insulin iva the peritoneum and have a regulator integrated into the control unit which controls the insulin pump as a factor of the measured values in such a way that the desired blood sugar levels are maintained.

A further object of the invention is achieved by means of a device of the same generic type for measuring human blood sugar levels wherein provision is made for an ultrasonic generator with which ultrasonic waves can be emitted in such a way that the point of measurement can be freed of tissue particles deposited from the blood. Even if the device of the same generic type is designed as an implant, the point of measurement can be cleansed in this way by means of an ultrasonic generator located extracorporeally. For instance, it is conceivable that for every analysis, the computer unit evaluates the measured result on the basis of specified characteristics on the basis of which it can be determined whether the measurement process has been compromised as a result of contamination at the point of measurement. As soon as the measurement result has been falsified in an unacceptable manner as determined on the basis of the characteristics, an alarm signal is emitted, whereby it is indicated to the patient that it is necessary to have the point of measurement cleaned by means of the external device.

BRIEF DESCRIPTION OF THE DRAWINGS

Further details of the invention are discussed with reference to the drawing.

DETAILED DESCRIPTION OF THE INVENTION

Figure 1:
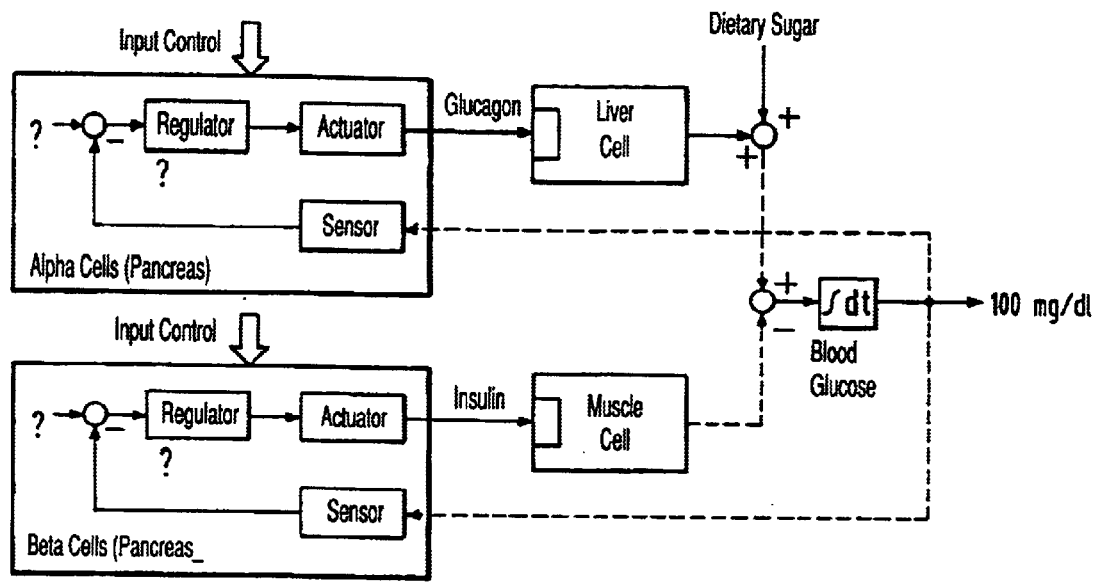
FIG. 1 is a schematic diagram showing the effect of insulin and glucagon on blood sugar levels.
Figure 2:
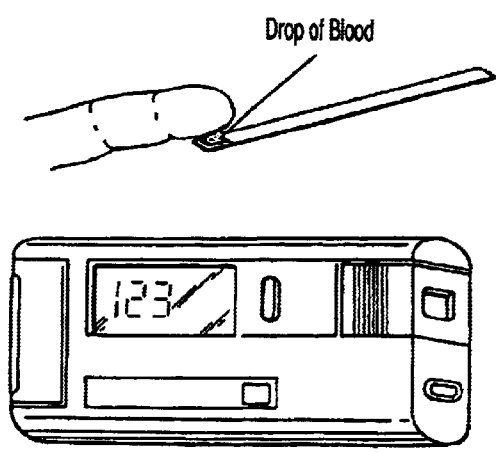
FIG. 2 is a schematic representation of a known testing device.
Figure 3:
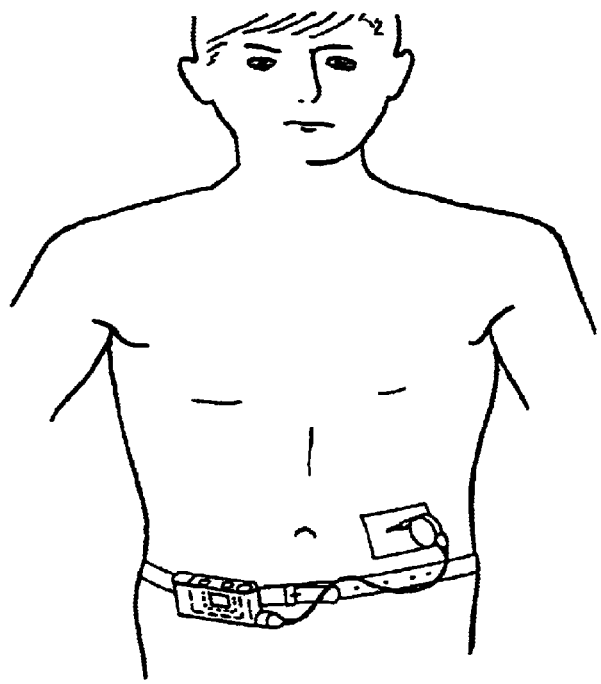
FIG. 3 shows an insulin pump attached to a patient.

FIGS. 1, 2, and 3 are previously described above.

Figure 4:
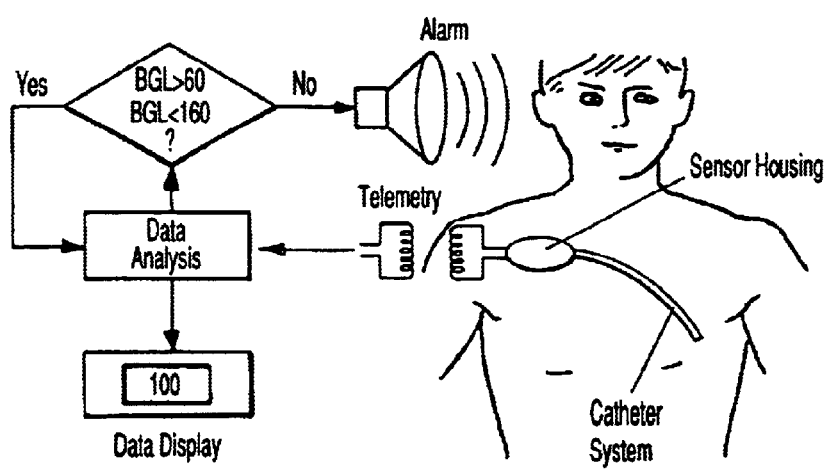
FIG. 4 shows the measurement system in accordance with the invention for continually determining blood sugar levels.

FIG. 4 shows the blood sugar measurement system in accordance with the invention.

The measurement system comprises of a sensor housing of biocompatible material (e.g. titanium) and a catheter system of biocompatible material (e.g. silicon) in contact with body fluids (e.g. blood). In addition, the measurement system comprises an extracorporeal transceiver unit with telemetry, data analyses, data representation and alarm functionality.

Figure 5:
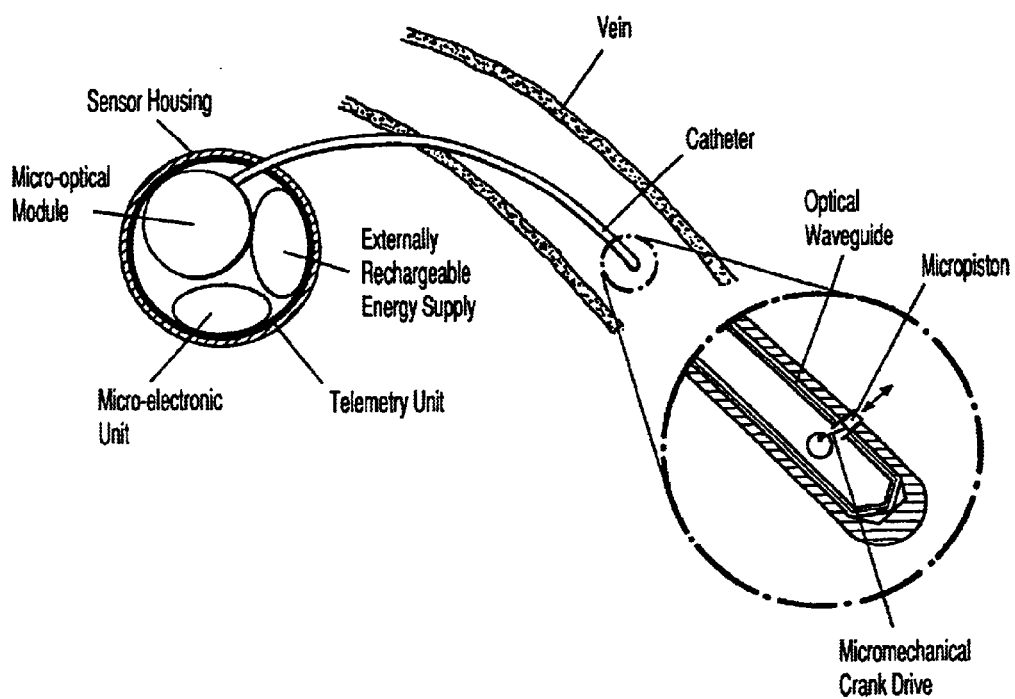
FIG. 5 shows the implant with a catheter which has an integrated optical waveguide and a micropiston at its free end.

FIG. 5 shows the implant with a catheter which has an integrated optical waveguide and a micropiston at its free end.

Several functional modules are integrated into the sensor housing:

transcutaneous telemetry unit for transmitting optical or electromagnetic data bidirectionally between the implanted sensor and the extracorporeal transceiver unit.

(externally chargeable) energy source integrated microelectronics/microcomputer to control all processes in the implant (measurements, signal analysis, telemetry, self-diagnosis, monitoring of battery function etc.

integrated micro-optical module for generating and measuring absorption, reflection and polarimetry of electromagnetic waves in various wavebands (e.g. visible light or near-infrared and mid-infrared light). Within a waveband it is possible to have various frequencies, for instance, by using several light sources micro-optical prisms or tuneable optical filters.

The catheter is multilumenal and contains one or more optical waveguides which carry the light from and to the micro-optical module in the sensor housing. Moreover, the catheter can also contain electrical lines for energy transmission, components for transferring mechanical energy (e.g. Bowden cable) or lumina for transferring hydraulic or pneumatic energy. The catheter is in contact with the body fluids (e.g. blood, peritoneal fluid or liquor) at the measurement points.

In the case of absorption and polarimetry measurement, light of various frequencies is conducted longitudinally along a constant sampling path through the measurement sample sequentially. To achieve this the sample volume is drawn into the catheter prior to measurement by a movable, tightly sealing micropiston and expelled after measurement. A micromechanical crank drive can be used to generate the piston's movement.

Also conceivable are mechanical, hydraulic, pneumatic or thermopneumatic elements for generating movement. The movement of the piston causes the light input and emission points to be cleansed automatically and prevents the blood from clotting or protein from being deposited along the sampling length. Moreover, if occurring at sufficiently frequent time intervals (e.g. every 10 minutes), the movement of the piston ensures that no fibrinous pseudo-membrane can form in the blood directly along the sampling length.

In the case of reflection spectroscopy, the path through the measurement sample does not need to he constant. Rather, the light is transmitted from the catheter into the fluid using suitable micro-optics and dispersed in a diffuse manner. A second micro-optical device is employed to absorb part of the dispersed light and transmitted back to the sensor housing. In order to prevent the formation of deposits and pseudo-membranes over the micro-optical device, there is also the option of cleansing the light input and emission points by means of a movable piston. The cleansing of the micro-optics by the ultrasonic transducer is also possible. If the catheter is positioned appropriately (right atrium of the heart as for cardiac pacemakers), the movement of the triscuspid valve cusp can also be used like a "windscreen wiper".

In order to increase the measurement accuracy and reliability, all three measurement procedures (absorption, reflection and polarimetry) can be combined in a suitable manner and weighted accordingly.

The sensor housing is sufficiently small and can typically be implanted in a pocket of tissue below the clavicle (subclavical, typical implantation location for cardiac pacemakers) or in the umbilical subcutaneous fatty tissue.

Figure 6:
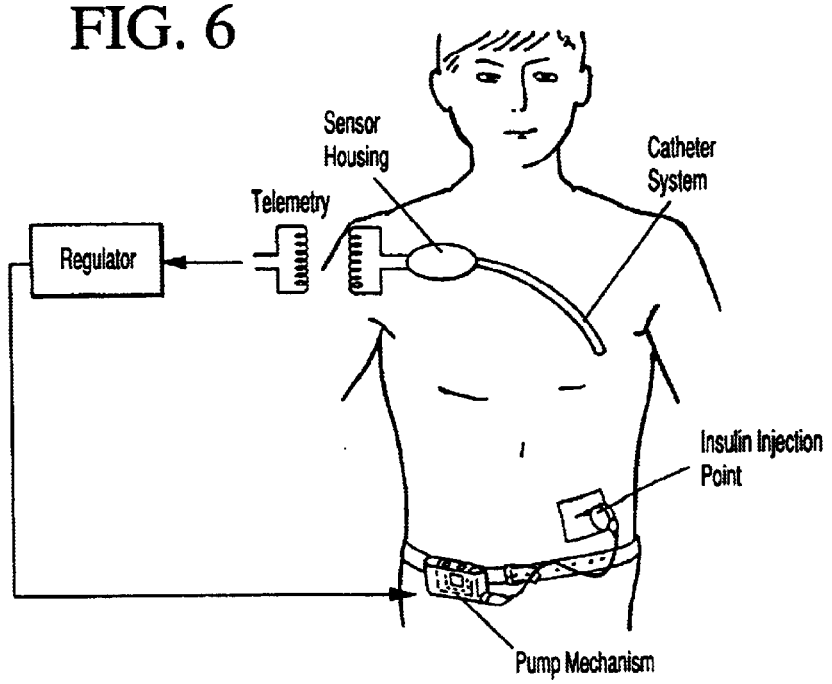
FIG. 6 shows the application of the implant in accordance with the invention in a closed feedback loop.

FIG. 6 shows the application of the implant in accordance with the invention in a closed feedback loop. The micro-optic blood sugar measurement system (implanted catheter and implanted sensor housing and external transceiver unit) can of course be used in addition to the monitoring function to close the defect blood sugar feedback loop. As a rule, the measurement system is combined with a control algorithm and appropriate extracorporeal hardware (electronics and pump mechanics).

Figure 7:
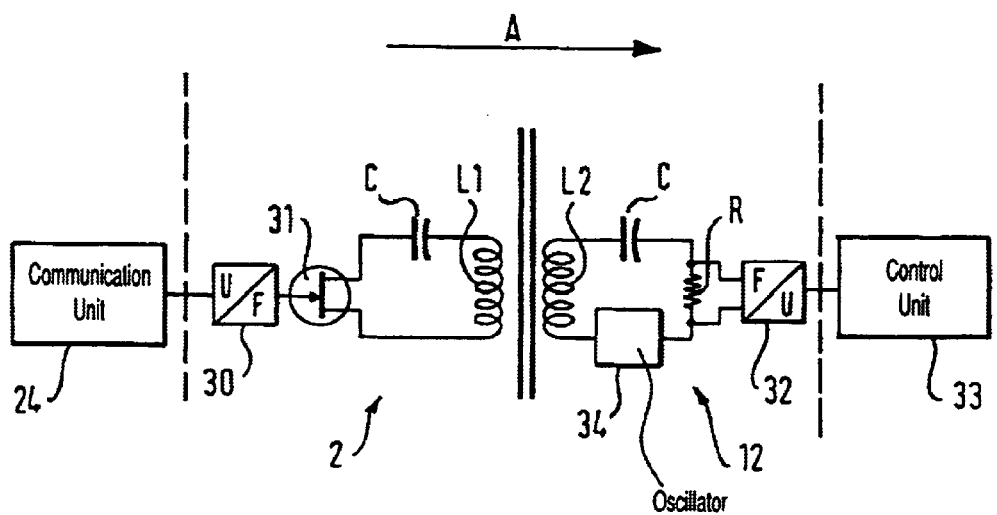
FIG. 7 shows a schematic circuit diagram for transferring data from the telemetry unit located in the implant to the control unit.

FIG. 7 shows an electrical schematic circuit diagram for data transmission from the telemetry unit located in the implant to the control unit. The direction of transmission is indicated by Arrow A. The values transformed in the communication unit 24 are fed to the probe and there to a voltage frequency converter 30 which clocks a transistor switch 31 as a result of which the resonant frequency of the oscillatory circuit formed by C and L1 is modified in accordance with the clock frequency. In the probe, this causes the resonant frequency of the oscillatory circuit generated by C and L2 to be tuned, whereby the transmitter energy is provided by the oscillator 34 located in the probe 12. This modulated resonant frequency is fed to the control unit 33 via the resistor R and the frequency voltage converter in the form of an analogue voltage.

Figure 8:
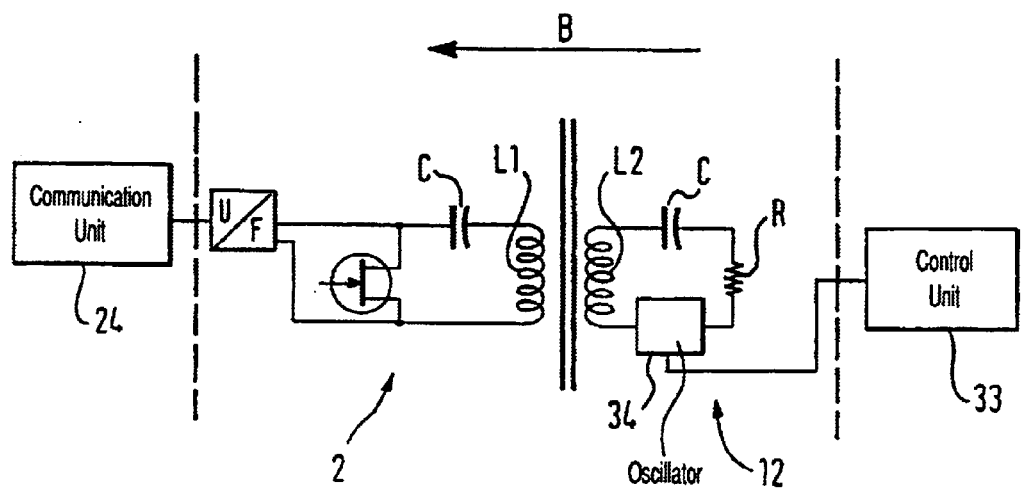
FIG. 8 shows a schematic circuit diagram for transferring data from the control unit to the telemetry unit located in the implant.

FIG. 8 shows a basic electrical circuit diagram for data transmission from the control unit to the telemetry unit in the implant. The direction of transmission is indicated by the direction of Arrow B. In this case the frequency of the oscillator 34 is modified in accordance with the values to be transmitted from the control unit. Transmission takes place in every other respect in the same way as in FIG. 3.

Figure 9:
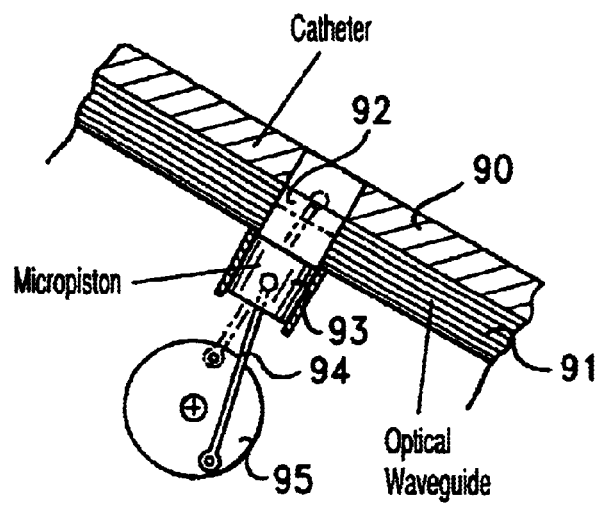
FIG. 9 shows an enlarged representation of the micromechanical crank drive in accordance with FIG. 5.

FIG. 9 shows an enlarged representation of the micromechanical crank drive in accordance with FIG. 5. The optical waveguide 91 is clad directly with a biocompatible material 90, whereby the transmission measurement is taken at the measurement point 92. The measurement point 92 can be cleansed by the form-fitting movement of the piston 91, whereby the piston 93 is actuated by means of a connecting rod 94 driven by a crank disk 95. The crank disk 95 can either be actuated directly by a micromotor or extracorporeally by the transmission of energy to the crank disk. In the case of the extracorporeal transmission of energy it is conceivable, for instance, that the crank disk 95 is fitted with magnets accordingly so that the crank disk follows an externally located, rotating magnetic field in a corresponding rotational manner.

Figure 10:
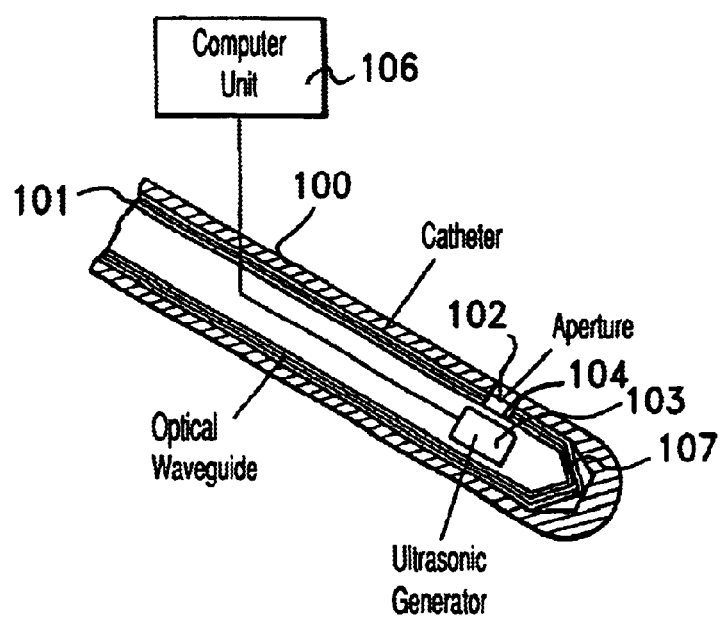
FIG. 10 shows the device in accordance with the invention with an ultrasonic generator

FIG. 10 shows the device in accordance with the invention with an ultrasonic generator anterior to the point of measurements. The catheter 100 also consists of biocompatible material on the internal wall of which an optical waveguide is attached. There is a gap in the optical waveguide at the point of measurement 102 so that the blood located there can be subjected to transmission measurement. At the end of the catheter at the point 107 the optical waveguide is bent in such a manner in order to improve the redirection of the light beam. Ahead of the point of measurement inside the catheter there is an ultrasonic generator 103 which is controlled by a computer unit 106. Provision can be made inside the catheter at the point of measurement 102 for a membrane 104 which can be caused to vibrate as a result of the impulse from the ultrasonic generator, whereby the point of measurement 102 is cleansed of tissue particles deposited from the blood, It is also conceivable that the ultrasonic generator is located directly on the inside wall of the optical waveguide so that the shock waves are transmitted directly into the point of measurement 102.

Figure 11:
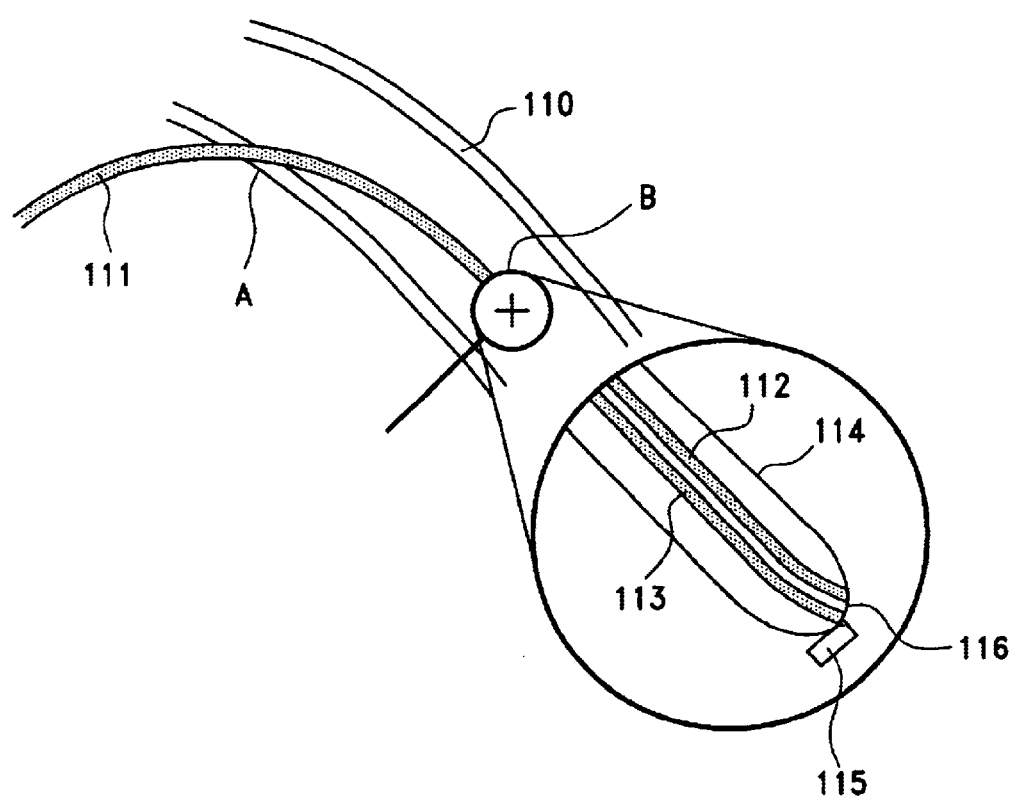
FIG. 11 shows the device in accordance with the invention with two optical waveguides and measurement based on diffuse reflection.

FIG. 11 shows the device in accordance with the invention on the basis of diffuse reflection. The catheter 111 is inserted into a blood vessel 110 at point A. The free end B of the catheter is shown in an enlargement. Accordingly, the catheter consists of cladding 114 of biocompatible material and two optical waveguides 112 and 113 running along the inside which are both laid parallel to the point of measurement 116. Provision is made at the end of the point of measurement 116 for a cleansing device 115, which can be of a design as indicated above.

What is claimed is:

1. Apparatus for measuring human blood sugar levels, comprising:
    a catheter, the free end of which is to be positioned in a blood vessel, wherein the catheter comprises at least one optical waveguide,
    a light source for coupling light into the at least one optical waveguide,
    a point of measurement at the free end of the catheter at which point the light is emitted from the at least one optical waveguide, wherein the light is dispersed by the blood and/or transmitted through the blood and wherein the dispersed and/or transmitted light is coupled again into the at least one optical waveguide,
    a detector to receive the light which is returned,
    a computer unit for analysing the light received by the detector,
    a cleansing device located at the point of measurement for removing the tissue particles deposited from the blood,
    the cleansing device comprises a controllable actuator which frees or wipes clear a light emission orifice of the at least one optical waveguide when activated, and
    the cleansing device is controllable by the computer unit.

2. Apparatus according to claim 1, wherein a movement of the actuator is generated by a shape memory alloy, a thermopneumatic drive, an electrostatic drive (piezoelement) or a rotor.

3. Apparatus according to claim 1, wherein the energy required for control purposes is supplied to the point of measurement in electrical, thermal, optical, mechanical, hydraulic or pneumatic form.

4. Apparatus according to claim 1, wherein the measurement at the point of measurement is undertaken by means of transmission (irradiation over a specified sampling length) or by means of diffuse reflection from the surface of the catheter.

5. Apparatus according to claim 1, wherein the catheter is clad with a biocompatible material.

6. Apparatus according to claim 5, wherein the catheter and the optical waveguide are designed as a single piece of solid material.

7. Apparatus according to claim 1, wherein the light source, the detector and the computer unit are integrated into an implant together with an energy store for providing voltage.

8. Apparatus according to claim 7, wherein a telemetry unit is integrated into the implant with which it is possible to transmit data and/or energy between the computer unit and a control unit located extracorporeally, wherein for that purpose a probe is connected to the control unit.

9. Apparatus according to claim 8, wherein the telemetry unit and the probe have an oscillatory circuit each with an inductor, wherein the oscillatory circuit on the side of the telemetry unit and the oscillatory circuit on the side of the probe can be tuned for the transmission of data and wherein the data are transmitted without direct contact by coupling the inductors inductively.

10. Apparatus according to claim 8, wherein the energy content of the frequency transmitted by the control unit to the telemetry unit charges an accumulator or a capacitor for the purpose of providing energy to the implant.

11. Apparatus for measuring human blood sugar levels, comprising:
   a catheter, the free end of which is to be positioned in a blood vessel, wherein the catheter comprises at least one optical waveguide,
   a light source for coupling light into the at least one optical waveguide,
   a point of measurement at the free end of the catheter at which point the light is emitted from the at least one optical waveguide, wherein the light is dispersed by the blood and/or transmitted through the blood and wherein the dispersed and/or transmitted light is coupled again into the at least one optical waveguide,
   a detector to receive the light which is returned,
   a computer unit for analysing the light received by the detector,
   a cleansing device located at the point of measurement for removing the tissue particles deposited from the blood, and
   the cleansing device comprises a controllable actuator, which comprises a piston which is inserted into a form-fitting opening located at the free end of the catheter and which moves between a position where the piston forms a seal flush with the catheter surface and a position where the piston fits into a recess located opposite the catheter surface, and that in the recessed position a light emission orifice of the at least one optical waveguide becomes free.

12. Apparatus according to claim 11, wherein a movement of the actuator is generated by a shape memory alloy, a thermopneumatic drive, an electrostatic drive (piezoelement) or a rotor.

13. Apparatus according to claim 11, wherein the piston is guided radially within the catheter.

14. Apparatus according to claim 11, wherein the piston is guided axially within the catheter.

15. Apparatus according to claim 11, wherein the piston is actuated by a micromotor with a crank.

16. Apparatus according to claim 11, wherein the piston is actuated by a lifting magnet.

17. Apparatus according to claim 11, wherein the energy required for control purposes is supplied to the point of measurement in electrical, thermal, optical, mechanical, hydraulic or pneumatic form.

18. Apparatus according to claim 11, wherein the measurement at the point of measurement is undertaken by means of transmission (irradiation over a specified sampling length) or by means of diffuse reflection from the surface of the catheter.

19. Apparatus according to claim 11, wherein the catheter is clad with a biocompatible material.

20. Apparatus according to claim 19, wherein the catheter and the optical waveguide are designed as a single piece of solid material.

21. Apparatus according to claim 11, wherein the light source, the detector and the computer unit are integrated into an implant together with an energy store for providing voltage.

22. Apparatus according to claim 21, wherein a telemetry unit is integrated into the implant with which it is possible to transmit data and/or energy between the computer unit and a control unit located extracorporeally, wherein for that purpose a probe is connected to the control unit.

23. Apparatus according to claim 22, wherein the telemetry unit and the probe have an oscillatory circuit each with an inductor, wherein the oscillatory circuit on the side of the telemetry unit and the oscillatory circuit on the side of the probe can be tuned for the transmission of data and wherein the data are transmitted without direct contact by coupling the inductors inductively.

24. Apparatus according to claim 22, wherein the energy content of the frequency transmitted by the control unit to the telemetry unit charges an accumulator or a capacitor for the purpose of providing energy to the implant.

25. Apparatus for measuring human blood sugar levels, comprising:
   a catheter, the free end of which is to be positioned in a blood vessel, wherein the catheter comprises at least one optical waveguide,
   a light source for coupling light into the at least one optical waveguide,
   a point of measurement at the free end of the catheter at which point the light is emitted from the at least one optical waveguide, wherein the light is dispersed by the blood and/or transmitted through the blood and wherein the dispersed and/or transmitted light is coupled again into the at least one optical waveguide,
   a detector to receive the light which is returned,
   a computer unit for analysing the light received by the detector,
   a cleansing device located at the point of measurement for removing the tissue particles deposited from the blood, and
   the cleansing device comprises a controllable actuator which frees or wipes clear a light emission orifice of the at least one optical waveguide when activated, wherein a control action is achieved by means of a hydraulic or pneumatic line.

26. Apparatus according to claim 25, wherein the measurement at the point of measurement is undertaken by means of transmission (irradiation over a specified sampling length) or by means of diffuse reflection from the surface of the catheter.

27. Apparatus according to claim 25, wherein the catheter is clad with a biocompatible material.

28. Apparatus according to claim 27, wherein the catheter and the optical waveguide are designed as a single piece of solid material.

29. Apparatus according to claim 25, wherein the light source, the detector and the computer unit are integrated into an implant together with an energy store for providing voltage.

30. Apparatus according to claim 29, wherein a telemetry unit is integrated into the implant with which it is possible to transmit data and/or energy between the computer unit and a control unit located extracorporeally, wherein for that purpose a probe is connected to the control unit.

31. Apparatus according to claim 30, wherein the telemetry unit and the probe have an oscillatory circuit each with an inductor, wherein the oscillatory circuit on the side of the telemetry unit and the oscillatory circuit on the side of the probe can be tuned for the transmission of data and wherein the data are transmitted without direct contact by coupling the inductors inductively.

32. Apparatus according to claim 30, wherein the energy content of the frequency transmitted by the control unit to the telemetry unit charges an accumulator or a capacitor for the purpose of providing energy to the implant.

33. Apparatus for measuring human blood sugar levels, comprising:

- a catheter, the free end of which is to be positioned in a blood vessel, wherein the catheter comprises at least one optical waveguide,
- a light source for coupling light into the at least one optical waveguide,
- a point of measurement at the free end of the catheter at which point the light is emitted from the at least one optical waveguide, wherein the light is dispersed by the blood and/or transmitted through the blood and wherein the dispersed and/or transmitted light is coupled again into the at least one optical waveguide,
- a detector to receive the light which is returned,
- a computer unit for analysing the light received by the detector,
- a cleansing device located at the point of measurement for removing the tissue particles deposited from the blood, wherein the cleansing device comprises a controllable actuator which frees or wipes clean a light emission orifice of the at least one optical waveguide when activated,
- the detector and the computer unit are integrated into an implant together with an energy store for providing voltage,
- a control unit located extracorporeally for regulating human blood sugar levels, wherein measured values are transmitted by a telemetry unit to said control unit,
- an extracorporeal insulin pump for injecting insulin through the peritoneum, and
- a regulator integrated into the control unit which controls the insulin pump subject to the measured values in such a way that the desired blood sugar level is attained.

34. Apparatus according to claim 33, wherein a movement of the actuator is generated by a shape memory alloy, a thermopneumatic drive, an electrostatic drive (piezoelement) or a rotor.

35. Apparatus according to claim 33, wherein the energy required for control purposes is supplied to the point of measurement in electrical, thermal, optical, mechanical, hydraulic or pneumatic form.

36. Apparatus according to claim 33 wherein the measurement at the point of measurement is undertaken by means of transmission (irradiation over a specified sampling length) or by means of diffuse reflection from the surface of the catheter.

37. Apparatus according to claim 33 wherein the catheter is clad with a biocompatible material.

38. Apparatus according to claim 37, wherein the catheter and the optical waveguide are designed as a single piece of solid material.

39. Apparatus according to claim 33, wherein the light source is integrated into the implant.

40. Apparatus according to claim 39, wherein a telemetry unit is integrated into the implant with which it is possible to transmit data and/or energy between the computer unit and a control unit located extracorporeally, wherein for that purpose a probe is connected to the control unit.

41. Apparatus according to claim 40, wherein the telemetry unit and the probe have an oscillatory circuit each with an inductor, wherein the oscillatory circuit on the side of the telemetry unit and the oscillatory circuit on the side of the probe can be tuned for the transmission of data and wherein the data are transmitted without direct contact by coupling the inductors inductively.

42. Apparatus according to claim 40, wherein the energy content of the frequency transmitted by the control unit to the telemetry unit charges an accumulator or a capacitor for the purpose of providing energy to the implant.

* * * * *